United States Patent
Brereton et al.

(10) Patent No.: US 6,408,698 B1
(45) Date of Patent: Jun. 25, 2002

(54) SENSORS AND METHOD FOR MEASUREMENT OF FLOW RATES AND CUMULATIVE FLOW IN DUCTS

(75) Inventors: Giles J. Brereton, Williamston; Harold J. Schock, Okemos; Ruby N. Ghosh, Okemos; Fathi M. Salam, Okemos, all of MI (US)

(73) Assignee: Board of Trustees Operating - Michigan State University, East Lansing, MI (US)

( * ) Notice: Subject to any disclaimer, the term of this patent is extended or adjusted under 35 U.S.C. 154(b) by 0 days.

(21) Appl. No.: 09/387,543

(22) Filed: Aug. 31, 1999

Related U.S. Application Data

(60) Provisional application No. 60/099,108, filed on Sep. 3, 1998.

(51) Int. Cl.[7] .............................. G01N 3/24; G01F 1/28
(52) U.S. Cl. ..................................... 73/841; 73/861.74
(58) Field of Search .......................... 73/841, 862.392, 73/862.581, 862.582, 204.26, 861.74, 861.73, 861.71

(56) References Cited

U.S. PATENT DOCUMENTS

| | | | | |
|---|---|---|---|---|
| 4,633,578 A | * | 1/1987 | Aine et al. | 73/204 |
| 4,864,724 A | * | 9/1989 | Bergstrom | 29/854 |
| 4,870,745 A | | 10/1989 | Lee | |
| 4,884,443 A | | 12/1989 | Lee et al. | |
| 5,237,084 A | | 8/1993 | Oliver et al. | |
| 5,237,867 A | * | 8/1993 | Cook, Jr. | 73/204.15 |
| 5,327,894 A | * | 7/1994 | Thomas | 73/861.25 |
| 5,524,084 A | | 6/1996 | Wang et al. | |
| 6,055,869 A | * | 5/2000 | Stemme et al. | 73/861.71 |

* cited by examiner

*Primary Examiner*—Max Noori
*Assistant Examiner*—Maurice Stevens
(74) *Attorney, Agent, or Firm*—Harness, Dickey & Pierce, P.L.C.

(57) ABSTRACT

The present invention relates to a sensor for measuring the instantaneous rate of mass flow and the cumulative mass flow in steady or unsteady flows of single-phase liquids or gases in a duct. By measuring the shear stress or the streamwise pressure gradient at the duct wall, and relating it to mass flow through solutions to the Navier Stokes equations of fluid mechanics, information on mass flow through the entire duct cross sectional area is deduced.

18 Claims, 4 Drawing Sheets

US 6,408,698 B1

SENSORS AND METHOD FOR MEASUREMENT OF FLOW RATES AND CUMULATIVE FLOW IN DUCTS

This application claims benefit of Provisional Application No. 60/099108 Sep. 3, 1998.

BACKGROUND OF THE INVENTION

1. Field of the Invention

The present invention relates to a sensor for measurement of the instantaneous rate of mass flow and the cumulative mass flow, in steady or unsteady flows, of single-phase liquids or gases along ducts.

2. Discussion of the Prior Art

The principal criterion for a successful design of a mass flow sensor is that it provides accurate measurements (e.g. ±0.5%) of the momentary mass-flow rate in steady and unsteady flows. In certain applications, the criterion that it measure accurately the cumulative mass flow (e.g. ±1.0%) over a specified time interval is more appropriate.

For example, in today's automobile engine, the device used most widely to measure the mass flow rate ṁ of air into the engine is the mass airflow sensor. The known mass airflow sensor generally comprises a "hot-wire" sensor housed in the center of a section of a duct as illustrated in FIG. 1 wherein the hot-wire sensor indicates the fluid speed |V| at the duct center.

When the momentary fluid speed is multiplied by the duct cross sectional area A and by the average fluid density ρ (inferred from other measurements of air temperature and pressure), a measure of the mass flow rate m=ρA|V| can be made. In this approach, the implicit assumption that the density across the flow is constant is quite reasonable in engine intake flows. A second implicit assumption, i.e., that the velocity at the duct center is also the velocity over the entire cross sectional area, is not completely valid and so A is replaced with an "effective" area $A_{eff}$ determined from a steady flow calibration experiment. More significantly, the hot wire sensor infers fluid speed according to the convective heat transfer from the wire and cannot distinguish the direction of the flow.

Since many ducts flows, and particularly those in intakes to internal combustion engines, are not unidirectional but can momentarily reverse, this existing method may result in incorrect readings of mass flow rate. Consequently, control of the proportions of air and fuel supplied to the engine can be compromised.

Variations on the above described method involve mounting the hot wire sensor within a bypass tube positioned in the duct to damp out unsteadiness in part of the flow, in an effort to remove the directional ambiguity. The presence of the tube obstructs the flow and changes the flow field, necessitating calibration experiments to determine $A_{eff}$, though in reality $A_{eff}$ then becomes a function of time and of the unsteadiness of the particular flow. A schematic of a prior art mass airflow sensor with a bypass duct is shown in FIG. 1.

In addition to the foregoing, venturi and orifice meters are known which measure mass flow rates based on an independent measurement of density and assumptions of steady flow. However, these types of meters are considered to be inadequate in non-steady flows. Turbine meters and moving vane devices also require an independent measure of density and have frequency responses which are too low for automotive intake applications, as well as being intrusive to the flow. Coriolis meters, which have high frequency responses and measure mass flow rate in direct proportion to the Coriolis force, impose large pressure drops on the flow and are most suitable for liquid flow applications.

As such, there is a need in the art for sensors capable of measuring instantaneous rates of mass flow and cumulative mass flow which are non-intrusive.

SUMMARY OF THE INVENTION

According to the present invention, the flow rate is determined by measuring a surface force such as the fluid shear stress $\tau_w$ or the streamwise pressure gradient $\partial p/\partial x$ with a sensor of the present invention. While the sensor is preferably enclosed within a duct, the duct itself may be of various cross-sectional shapes, i.e., round, square, eliptical, convoluted, etc. By deducing the flow rate ṁ or cumulative mass flow $m_{cum}$ from a fluid-mechanics relationship between the mass-flow rate and the measured shear stress, the fluid stress and/or streamwise pressure gradient can be obtained. For fully developed, unsteady, laminar, axisymmetric flow of a Newtonian fluid, these relationships are of the form:

$$\dot{m} \int_0^t \left(-\frac{\partial p}{\partial x}(t')\right) \cdot f(t-t')dt'$$

$$m_{cum} = \frac{R^2}{v} \int_0^{t_{cum}} \left(-\frac{\partial p}{\partial x}(t')\right) \cdot g(t-t')dt'$$

or $$\dot{m} = R \int_0^t \tau_w(t') \cdot h(t-t')dt'$$

$$m_{cum} = \frac{R^3}{v} \int_0^{t_{cum}} \tau_w(t') \cdot j(t-t')dt'$$

where t is time, R is the duct radius, v is the fluid kinematic viscosity, $\partial p/\partial x$ is the streamwise pressure gradient, and f g, h, and j are smoothly varying mathematical functions. Processing of shear-stress or pressure gradient measurements with either of these relationships, which involve convolution integrals, are carried out in real-time using an integrated analog-electronics circuit. In specific applications of this kind, where functions f, g, h, and j are known, analog circuits can have higher processing speeds than digital ones. While either shear stress or the pressure gradient could be used as the sensed variable in flows which are fully developed at the sensor location, it is necessary to sense shear stress when the unsteadiness in the flow past the sensor is wave-like.

When compared to the hot-wire mass-airflow sensor used in today's automobile engine, the present has the advantages that: i) it is wall mounted and therefore non-intrusive to the flow; ii) it can be combined easily with other sensors; iii) it can measure mass-flow rate without requiring an independent measurement of density; and iv) it measures the direction of the flow. Further, when contrasted with orifice meters, the present invention has the advantages of performing accurately in unsteady flow and being able to measure flow direction. When compared with Coriolis meters, the present invention has the advantage that it does not impose a large pressure drop on the flow.

One application for the sensor and methods of the present invention is that automotive engine manufacturers could use the sensor in place of existing mass-airflow sensors in engines as well as for measuring flow rates of mixtures of air, exhaust gases and hydrocarbon vapors in engine intake systems. Still another perceived application for the sensor of the present invention is the measurement of pulmonary flows and other unsteady duct flows in which a surface mounted sensor is preferred.

DETAILED DESCRIPTION OF THE INVENTION

Figure 1:
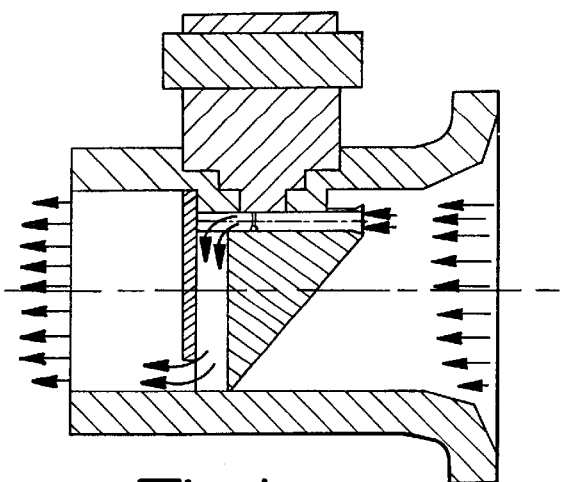
FIG. 1 is a side elevation view of a central section through a prior art "hot wire" sensor.
Figure 1A:
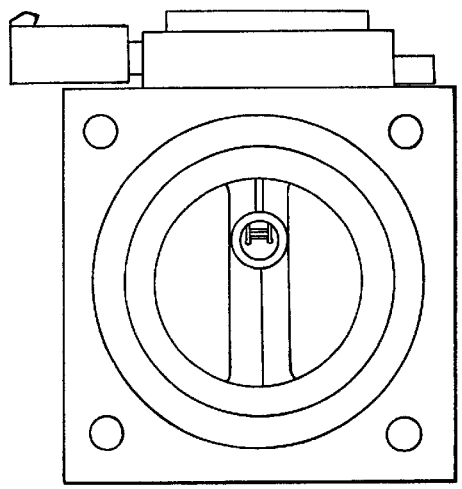
FIG. 1A is an end view of the prior art hot wire sensor of FIG. 1.
Figure 2:
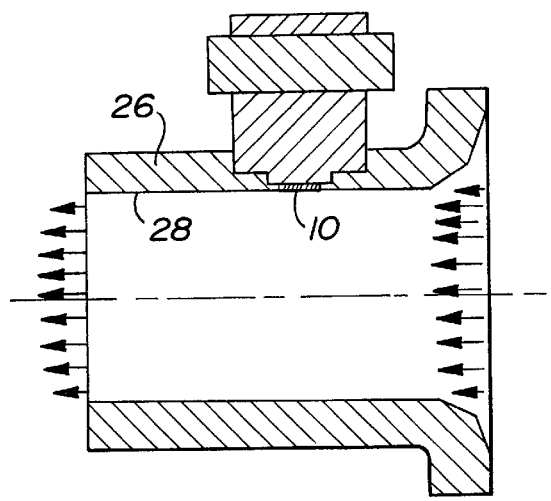
FIG. 2 is a side elevation view illustrating the sensor of the present invention.
Figure 2A:
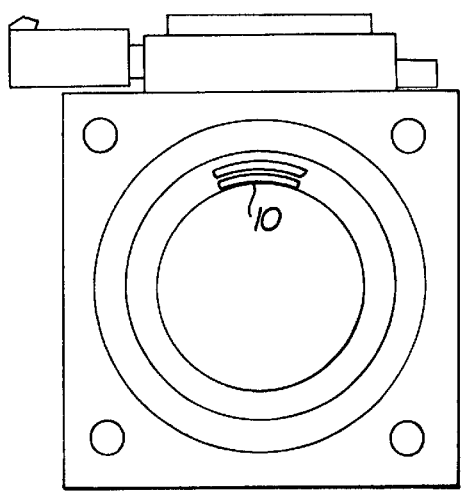
FIG. 2A is an end view of the sensor of FIG. 2.

Referring to FIGS. 2 and 2A, the sensor 10 of the present invention, which preferably is formed from a silicon or polysilicon, comprises a support member 12 and a floating pad 14. The floating pad 14 is etched out of the support member 12 utilizing known micromachining techniques to ensure that an exposed surface 16 of the sensor along both the support member 12 and the floating pad 14 are disposed along the same plane. As a result of the etching, the sensor 10 includes a lateral gap 18 occurring between the support member 12 and floating pad 14 which is on the order of 0.1 mm and a vertical gap 20. Thus, the floating pad 14 is suspended by tethers or coupling members 22 occurring in relative proximity to the perimeter or edge 24 of the pad.

Figure 3:
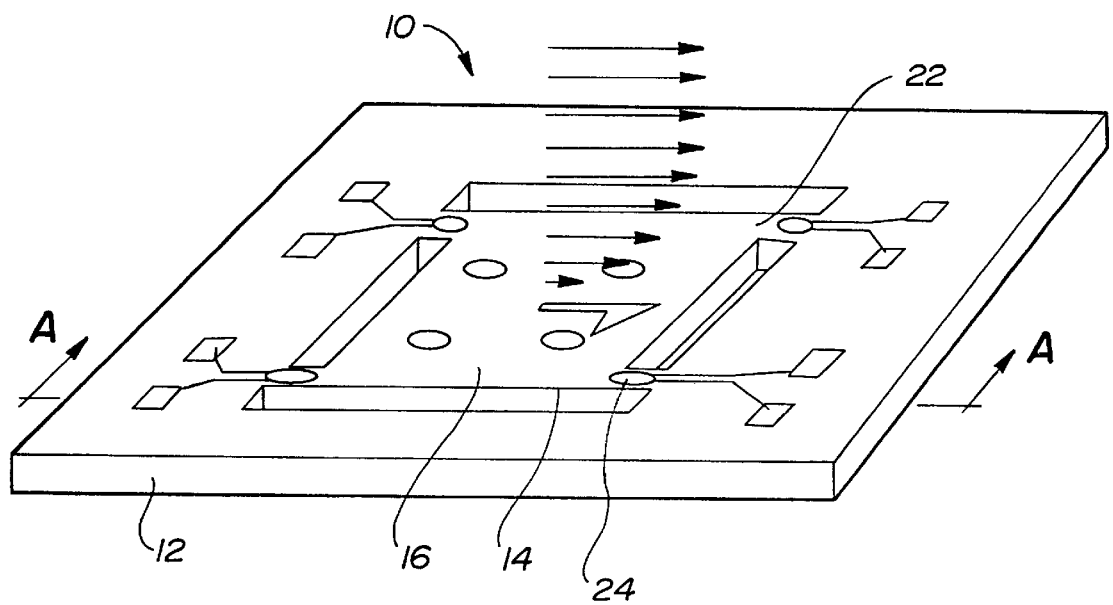
FIG. 3 is an elevational view illustrating the shear stress sensor of the present invention.
Figure 3A:
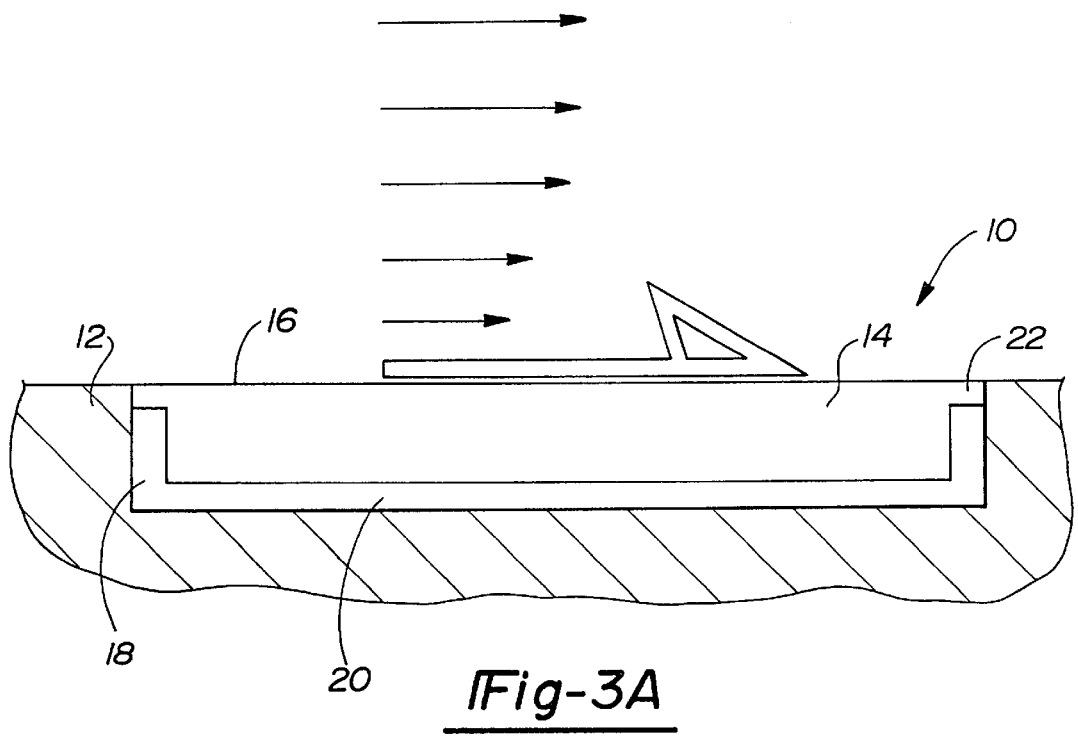
FIG. 3A is a cross sectional view of the sensor of FIG. 2 taken at line A—A.

To implement the sensor 10 as a shear stress sensor, i.e., for flows in which the streamwise velocity varies with streamwise distance at the plane of the sensor such as, for example, along an interior surface 28 of a duct 26, the fluid shear stress acting on the floating pad 14 is measured as a function of the difference between the extensional and compressional strain of the tethers 22, using area ratios and the Young's modulus for the tether material to relate strain to stress. To measure strains, the tethers 22 are equipped with a semiconductor piezo-resistive strain gauge as shown in FIG. 3 or optionally with a piezo-tunneling (reverse-bias $n^{++}/p^+$ or $p^{++}/n^+$ junction) strain sensor (not shown) adhered to the top surface of or fabricated within each tether at position 24 as shown in FIG. 3. A suitable commercially available piezoelectric pressure sensor is Data Instruments Corp., Model DUXL 20D 7C21-7.

When there is flow past the sensor 10, a shear force acts on the exposed surface 16 of the floating pad. This shear force is equal to the shear stress imparted by the streamwise fluid velocity when integrated over the pad's upper surface area. Thus, larger pads produce greater shear forces but reduce the spatial resolution of the sensor. In equilibrium, the shear force acting on the sensor exposed surface is balanced by equal and opposite forces of tension/ compression, shared almost equally between each tether arm 22. The forces in each tether arm 22 divided by the tether cross-sectional area determine the tensile/compressive stresses in each tether arm, with smaller cross-sectional areas resulting in larger stresses. The strains measured by strain gauges attached to the tether arms 22 are the stresses divided by the Young's modulus of the tether-arm material. The cross-sectional area of the tether arms is chosen to be small enough to produce a measurable strain, yet large enough to resist failure through overloading, vibration and other external forces. Thus, the overall ratio of measured strain to applied shear stress is proportional to the ratio of pad surface area to tether-arm cross-sectional area. Other design considerations favor using as small a pad 14 as possible, to provide the fastest response to changing shear forces.

Preferably, in a strain gauge implementation, two strain gauges would be employed as the active arms of a Wheatstone bridge (temperature compensated). The remainder of the bridge circuit could be located on the support member 12 or external to the entire sensor assembly. In the event that a reverse bias junction sensor is employed, the difference in the currents through each junction would be measured by circuitry (described below) positioned predominately along the support member 12. This circuitry is described below (see attached pages).

The sensor 10, when utilized as a stress-strain instrument, can be employed singly to analyze axisymmetric flows or in an array to analyze circular asymmetric flows in a duct wall by way of non-limiting example.

Figure 4:
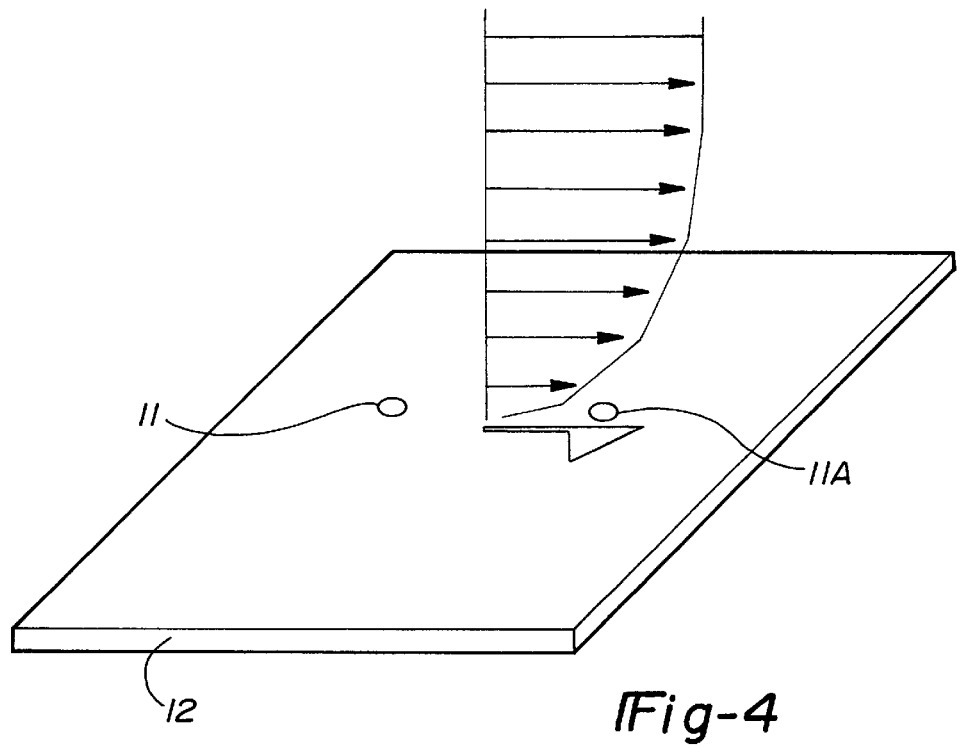
FIG. 4 is an elevational view of the sensor of FIG. 2 illustrating the position of the pressure sensors in relation to the velocity and shear force vectors.

Referring to FIG. 4, the sensor 10 is shown as being employed as part of a pressure-gradient sensor system for the measurement of mass-flow rates. According to this embodiment, two sensors 11 and 11A are positioned a pre-determined distance apart in order to measure the difference in pressure between the sensors 11 and 11A. As should be understood by those skilled in the art, pressure-gradient sensors are useful for flows in which streamwise velocity past the sensors does not vary with streamwise distance.

Referring to FIG. 2, the sensor 10 is shown being employed as part of a shear-stress sensor system for measuring mass flow rates. As should be understood by the foregoing description, the fluid stress acting on the pad is measured as a function of the difference between the extensional and compressional strains on the tethers using area ratios and Young's modulus for the sensor material, i.e., silicon or polysilicon to relate stress to strain.

To process the sensor signal, analog circuits which perform real time convolution integrals of sensor outputs for $\tau_\omega$ and $\partial P/\partial \kappa$ with functions f g, h and j are utilized. An example is given of the circuit which would perform the convolution integral for functions f and g, whose shapes approximate exponential decays or piecewise-exponential decays. The convolution integral circuit is designed for possible integration within the sensor microstructure. With minor variations, it can accept as its input signal either: i) a single absolute voltage between ground and the supply voltage (FIG. 5), as provided by reverse-bias piezo-tunneling strain sensors whose current difference is converted to a voltage; or ii) a differential voltage (FIG. 6), as supplied by a shear stress sensor with piezoresistive strain gages in two arms of a Wheatstone bridge, or supplied as the outputs from two pressure transducers.

Figure 5:
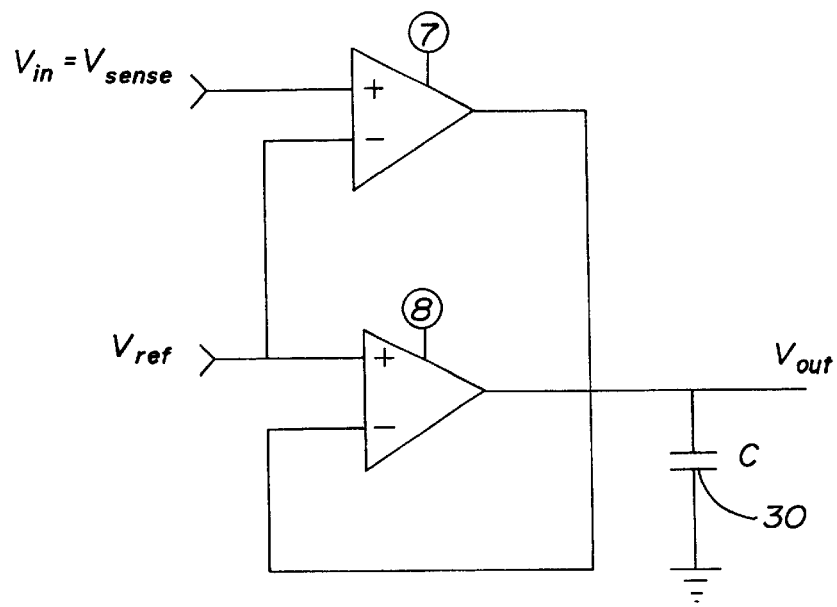
FIG. 5 is a schematic diagram illustrating a convolution integral circuit for single voltage inputs.
Figure 6:
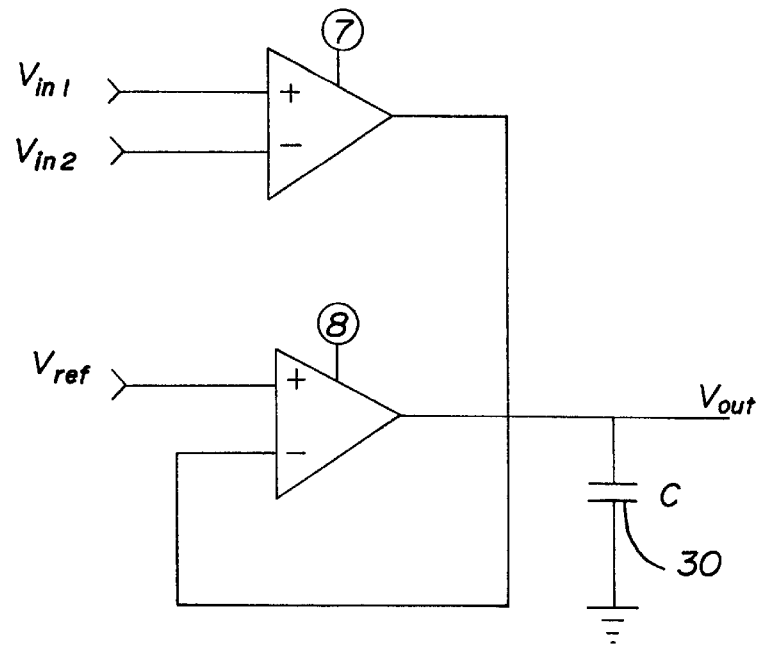
FIG. 6 is a schematic diagram illustrating a convolution integral circuit for differential voltage inputs.

The circuit shown in FIG. 5 carries out the convolution integral of input voltage $V_{in}$ with an exponentially decaying function, providing the result of the integral as voltage $V_{out}$. The circuit comprises two transconductance amplifiers and a capacitive element 30. The capacitive element 30 may be integrated within the sensor chip if design considerations allow it to be less than a few picofarads. Otherwise, a larger capacitance would require external mounting and connections. The standard transconductance amplifier, in CMOS or bipolar circuits, comprises a differential pair and a current mirror block. Typically, this can be achieved by 3 transistors for the differential pair and 2 to 6 transistors for the mirror(s).

The bias voltage of transconductance amplifier 1, applied at node 7 in FIG. 5, serves as a scaling factor for the input signal $V_{in}$. The bias voltage applied at node 8 of transconductance amplifier 2 controls the convolution circuit's impulse response.

The model equations governing this convolution circuit are $$C\frac{dV_{out}}{dt} = I_1 + I_2 = G_1(V_\epsilon - V_{ref}) - G_2(V_{out} - V_{ref})$$

where C is the capacitance. The "nonlinear" transconductance amplifier functions $G_1(\ )$ and $G_2(\ )$ approximate hyperbolic tangents with amplitudes that depends on the bias voltages at nodes 7 and 8 respectively, when operated in the subthreshold regions of CMOS transistors. By keeping the amplitudes below about 80 millivolts, functions $G_1$ and $G_2$ are restricted to the linear regions of the hyperbolic tangent functions and the bias voltage controlling $G_2$ serves to change the slope of $G_2$, effectively changing the exponent of the exponentially decaying impulse response. When the sensor output is a differential voltage, convolutions of the voltage difference $V_{in\ 1} - V_{in\ 2}$ with decaying exponential functions can be achieved with a similar circuit shown in FIG. 4B. These circuits are very efficient and consume only a fraction of a micro- or milli-watt when they operate in the subthreshold region.

Figure 7:
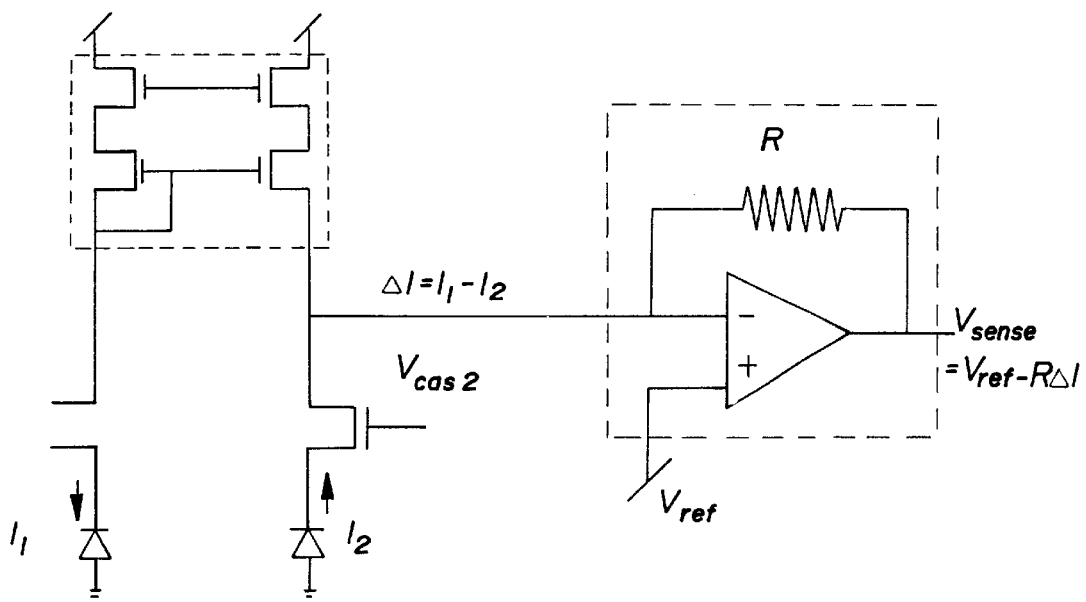
FIG. 7 is a schematic diagram of a circuit which converts the difference in currents in reverse-bias junctions into voltage.

If a wall shear stress is measured in terms of the difference between a compressive and a tensile strain, using reverse-bias piezo-tunneling strain sensors implanted on tether arms, a circuit is needed to convert the difference in small sensor currents $\Delta I = I_1 - I_2$ to the voltage input required for the convolution integral circuit. This current conversion circuit is shown in FIG. 7 and is also designed so it may be integrated as part of the sensor structure on a single chip or module. In this design, the piezo-tunneling junctions, which act as strain sensors, are connected via a current mirror which feeds the current difference $\Delta I$ to the sense-amp block. Two cascade transistors control the performance of the circuits via the bias voltages $V_{cas\ 1}$ and $V_{cas\ 2}$. In practice, one of the bias voltages ($V_{cas\ 1}$) may be fixed while the second one would be adjusted to optimize circuit performance. The measured current difference $\Delta I$ is fed to the sense amp block, which includes an operational amplifier and a large resistance R to scale the current difference. The governing equation of the overall circuit is:

$$V_{sense} = V_{ref} - R\Delta I.$$

Thus, the wall shear stress is measured in terms of the sensor currents $I_1$, and $I_2$, whose difference $\Delta I$ is processed as an amplified and offset voltage $V_{sense}$. This voltage may then be fed to the convolution integral circuit of FIG. 4A, the output voltage of which will be proportional to the momentary mass flow rate.

The sensors described herein can be used in conjunction with other types of sensors such as oxygen and hydrocarbon sensors for medical applications and semi-conductors or solid state sensors for the measurement of chemical composition, by way of non-limiting example.

As an example of the calculation of mass flow rate $\dot{m}(t)$ from measurements of wall shear stress $\tau_\omega(t)$ in an unsteady flow, we consider a pipe flow in which the measured shear stress oscillates back and forth as a sine wave at angular velocity $\omega$, or $\tau_\omega = \sin(\omega t)$. The $\dot{m} \sim \tau_\omega$ relation is written as:

$$\dot{m}(t) = R \int_0^t \tau_\omega(t')h(t-t')dt'$$

but can be equivalently written as $$\dot{m}(t) = R \int_o^t \frac{\partial \tau_w}{\partial t}(t')h_1(t-t')dt'$$

where the Laplace transform of $h_1$ is equal to the Laplace transform of h divided by s. If $h_1(t-t')$ is set equal to $\pi R^2/(4\nu) + \pi H_1(t-t')$ then $$\dot{m}(t) = \frac{\pi R^3}{4\nu}\tau_\omega(t) + \pi R \int_0^t \frac{\partial \tau_w}{\partial t}(t')H_1(t-t')dt'$$

Finally, if G is chosen so that its Laplace transform is equal to the Laplace transform of $H_1$ multiplied by s $$\dot{m}(t) = \frac{\pi R^3}{4\nu}\tau_\omega(t) + \pi R \int_0^t \tau_\omega(t')G(t-t')dt'$$

The first term in this expression is the steady flow result while the second term represents the extra effect of unsteadiness. For laminar fully-developed pipe flow, the function G will not have a simple analytical form, so we approximate it as a decaying exponential for the purposes of this example calculation. Thus we set $G(t-t_1) = e^{-(t-t')\nu/R^2}$, where the normalization by $R^2/\nu$ assures a proper dimensionless exponent. For this shear-stress history and function G, the $\dot{m} \sim \tau_\omega$ relation becomes:

$$\dot{m}(t) = \frac{\pi R^3}{4\nu}\tau_\omega(t) + \pi R \int_0^t \sin(\omega t')e^{-(t-t')\nu/R^2}dt'$$

The integration can be performed analytically to yield the result:

$$\dot{m}(t) = \frac{\pi R^3}{4\nu}\tau_\omega(t) + $$
$$\frac{\pi R^3}{\nu}\frac{1}{1+(\omega R^2/\nu)^2}\left[\sin(\omega t) - \frac{\omega R^2}{\nu}\cos(\omega t) + e^{-\nu t/R^2}\right]$$

This result, which includes unsteady effects, has an additional group of terms which makes it significantly different from the result which would be obtained using only steady-flow principles, which is:

$$\dot{m}(t) = \frac{\pi R^3}{4\nu}\tau_\omega(t)$$

If the exact function G, derived from solution of the Navier Stokes equations, were used, a similar result and a similar distinction between unsteady- and steady-flow analysis would be deduced.

While it will be apparent that the preferred embodiments of the invention disclosed are well calculated to fulfill the objects stated, it will be appreciated that the invention is susceptible to modification, variation and change without departing from the spirit thereof.

What is claimed is:

1. A sensing mechanism capable of measuring shear stress resulting from an unsteady mass flow along a duct, comprising:
   a support member disposed along an interior surface of said duct, said support member including a first exposed surface;
   a floating pad including a first exposed surface;
   a plurality of coupling members which suspend said floating pad over said support member, said coupling members including a first exposed surface wherein each of said exposed surfaces of said floating pad, support member and plurality of coupling members are disposed along a substantially common plane, with said interior surface of said duct;
   a plurality of sensors fixedly coupled to said plurality of coupling members capable of measuring strain within the coupling members; and
   a convolution integral circuit capable of accepting an output from said sensing mechanism and capable of performing a convolution integral with said surface force and a known mathematical function, such that said convolution integral provides a mass flow value, said known mathematical function representing a fluid-mechanical behavior of said unsteady mass flow.

2. The sensing mechanism of claim 1 wherein said plurality of sensors comprises a plurality of piezo-tunneling sensors.

3. The sensing mechanism of claim 1 wherein said plurality of sensors comprises a plurality of piezoresistive sensors.

4. A system capable of measuring unsteady mass flow along a duct, comprising:
   a sensing mechanism disposed along an interior surface of said duct capable of measuring a surface force, said surface force having a fluid-mechanics relationship with said mass flow, said sensing mechanism having
   a support member disposed along said interior surface of said duct, said support member including a first exposed surface;
   a floating pad including a first exposed surface;
   a plurality of coupling members which suspend said floating pad over said support member, said coupling members including a first exposed surface wherein each of said exposed surfaces of said floating pad, support member and plurality of coupling members are disposed along a substantially common plane, with said interior surface of said duct;
   a plurality of sensors positioned along said plurality of coupling members, said sensors being capable of measuring strain within said coupling members; and
   a convolution integral circuit capable of accepting an output from said sensing mechanism and capable of performing a convolution integral with said surface force and a known mathematical function, such that said convolution integral provides a mass flow value, said known mathematical function representing a fluid-mechanical behavior of said unsteady mass flow.

5. The system of claim 4 wherein said plurality of sensors comprises a plurality of piezo-tunneling sensors capable of generating a current difference in response to tension or compression, and said sensing mechanism further comprises a current conversion circuit capable of converting said current difference into an absolute voltage.

6. The system of claim 4 wherein said plurality of sensors comprises a plurality of piezoresistive sensors capable of changing resistances in response to tension or compression.

7. The system of claim 6 wherein said plurality of piezoresistive sensors serve as active arms to a Wheatstone bridge circuit, said Wheatstone bridge circuit being capable of converting said resistances into a differential voltage.

8. The system of claim 4 wherein said sensing mechanism comprises a plurality of pressure transducers capable of generating a differential voltage in response to said surface force.

9. The system of claim 4 wherein said convolution integral circuit comprises:
   a plurality of transconductance amplifiers and a capacitor which forms a circuit capable of producing a convolution integral to thereby provide an output proportional to said mass flow;
   a capacitive element and a bias voltage applied to each transductance amplifier to determine the shape of said convolution integral; and
   an input for providing at least one voltage to permit either an absolute or differential voltage input from said sensing element.

10. A method for determining unsteady mass flow along a duct, comprising the steps of:
    providing a sensing mechanism having a floating member supported by a plurality of coupling members, each coupling member having a sensor capable of measuring strain within said coupling member;
    measuring a strain having a fluid-mechanics relationship to said mass flow;
    determining a mathematical function which represents a fluid-mechanical behavior of said mass flow; and
    performing a convolution integral with said strain and said mathematical function, such that said convolution integral provides said unsteady mass flow value.

11. The method of claim 10 wherein said step of measuring said surface force comprises measuring shear stress.

12. The method of claim 11 wherein said step of measuring shear stress comprises:
    measuring a difference between extensional and compressional strain along an interior surface of said duct; and
    converting said difference between extensional and compressional strain to said shear stress.

13. The method of claim 10 wherein said step of measuring said surface force comprises measuring a pressure gradient.

14. The method of claim 13 wherein said step of measuring said pressure gradient comprises measuring a difference in pressure between a plurality of locations along an interior surface of said duct.

15. A sensor capable of measuring shear stress resulting from an unsteady fluid flow along a duct, comprising:
    a floating pad, cutting a first exposed surface;
    a plurality of members which support said floating pad, said coupling members including a first exposed surface, each of said exposed surfaces of said floating pad and coupling members are disposed along a substantially common plane, adjacent said interior surface of said duct;

a plurality of sensors fixedly coupled to said coupling member first exposed surface wherein said plurality of sensors is capable of measuring strain within said coupling members; and a convolution integral circuit connected to said sensing mechanism, said convolution integral circuit calculating said unsteady fluid flow value.

16. The sensor of claim 15 wherein said plurality of sensors comprises a plurality of piezo-tunneling sensors.

17. The sensor of claim 15 wherein said plurality of sensors comprises a plurality of piezo-resistive sensors.

18. The sensor of claim 15 comprising a convolution integral circuit capable of accepting an output from said sensors and capable of performing a convolution integral with said surface force and a known mathematical function, such that said convolution integral provides a mass flow value.

* * * * *

UNITED STATES PATENT AND TRADEMARK OFFICE
CERTIFICATE OF CORRECTION

PATENT NO. : 6,408,698 B1
DATED : June 25, 2002
INVENTOR(S) : Brereton et al.

It is certified that error appears in the above-identified patent and that said Letters Patent is hereby corrected as shown below:

<u>Title page,</u>
Item [56], References Cited, add -- 4,888,988, 12/1989, Lee et al. --

<u>Column 2,</u>
Line 36, delete "f g," and insert -- f, g, --.

<u>Column 4,</u>
Line 52, delete "∂P/∂k" should be -- ∂p/∂x --.
Line 52, delete "f g," and insert -- f, g, --.

<u>Column 6,</u>
Line 38, delete "$G(t-t_1)=e^{-(t-t')v/R^3}$" and insert -- $G(t-t')=e^{-(t-t')v/R^3}$ --.

<u>Column 8,</u>
Line 42, after "provides" delete "said" and insert -- an unsteady --.

Signed and Sealed this

Twenty-fifth Day of March, 2003

JAMES E. ROGAN
*Director of the United States Patent and Trademark Office*